United States Patent [19]

Ruschke

[11] Patent Number: 4,573,974
[45] Date of Patent: Mar. 4, 1986

[54] MEDICAL ADMINISTRATION SET ENABLING SEQUENTIAL DELIVERY OF TWO LIQUIDS AT DIFFERENT FLOW RATE

[75] Inventor: Rick Ruschke, McHenry, Ill.

[73] Assignee: Baxter Travenol Laboratories, Inc., Deerfield, Ill.

[21] Appl. No.: 726,928

[22] Filed: Apr. 25, 1985

Related U.S. Application Data

[63] Continuation of Ser. No. 445,872, Dec. 1, 1982, abandoned.

[51] Int. Cl.$^4$ ............................................. A61M 5/14
[52] U.S. Cl. ..................................... 604/81; 137/113
[58] Field of Search ............................. 137/112-114; 604/80-85; 222/145

[56] References Cited

U.S. PATENT DOCUMENTS

| 4,034,754 | 7/1977 | Virag | 128/214 R |
|---|---|---|---|
| 4,105,029 | 8/1978 | Virag | 128/214 R |
| 4,219,022 | 8/1980 | Genese | 128/214 G |
| 4,236,515 | 12/1980 | Genese | 604/81 |
| 4,237,879 | 12/1980 | Genese | 604/81 |
| 4,237,880 | 12/1980 | Genese | 128/214 G |
| 4,250,879 | 2/1981 | Muetterties | 128/214 G |
| 4,252,116 | 2/1981 | Genese et al. | 128/214 G |
| 4,256,104 | 3/1981 | Muetterties et al. | 128/214 G |
| 4,256,105 | 3/1981 | Leahey et al. | 128/214 G |
| 4,258,712 | 3/1981 | Harms et al. | 128/214 G |
| 4,324,238 | 4/1982 | Genese et al. | 128/214 G |

FOREIGN PATENT DOCUMENTS

2059776  4/1981  United Kingdom .

Primary Examiner—Dalton L. Truluck
Attorney, Agent, or Firm—Paul C. Flattery; Bradford R. L. Price; Kay H. Pierce

[57] ABSTRACT

A medical liquid administration set is disclosed for the sequential administration of two medical liquid sources which can be delivered at different liquid flow rates without readjustment of the administration set. The set includes first and second conduits for connection to first and second medical liquid sources, respectively. A cross-over branch places the second conduit in communication with the distal end of the first conduit. A common conduit extends downstream of the first conduit and cross-over branch. The common and second conduits are in communication at their downstream ends, just upstream of the set outlet. Separately adjustable liquid delivery rate control means are disposed on the common and second conduits to allow for separate delivery rates of the first and second liquid sources. One-way valves are disposed in the cross-over branch and the first conduit to permit liquid flow only in the downstream direction.

The administration set enables independent flow adjustment of the two liquid sources without readjustment of the set, without danger of patient air embolism and without a critical failure mode.

12 Claims, 4 Drawing Figures

MEDICAL ADMINISTRATION SET ENABLING SEQUENTIAL DELIVERY OF TWO LIQUIDS AT DIFFERENT FLOW RATE

This application is a continuation of application Ser. No. 06/445,872, filed Dec. 1, 1982 now abandoned.

TECHNICAL FIELD OF THE INVENTION

The present invention is related generally to the administration of medical liquids and is more particularly related to a medical liquid administration set for sequential intravenous administration of two medical liquid sources at different flow rates.

BACKGROUND OF THE INVENTION

In the intravenous administration of medical liquids to a patient, it is often desired to administer more than one medical liquid through a single venous puncture site. For example, a container of dextrose or saline solution may be administered through a parenteral administration set such as sold by Travenol Laboratories, Inc. of Deerfield, Illinois, identified as a CONTINU-FLO® set, such as Product Code Nos. 2C0123 and 2C0251. The downstream end of the administration set is connected to a venous catheter, such as a FLASH-CATH® catheter sold by Travenol Laboratories, identified by Product Code No. 2N1175.

A second medical liquid, in another source container, may be infused through the same puncture site and venous catheter by connecting the second container to a secondary medication administration set such as identified by Product Code No. 2C0418, sold by Travenol Laboratories. The other end of the secondary medication set has a needle which is inserted into an injection site on the primary CONTINU-FLO set.

Another system designed for the infusion of two medical liquids has been sold by Abbott Laboratories.

The advantage of such systems for infusing two medical liquid sources is that only a single entry point is made into the patient. Further, the nurse or other medical personnel need not engage in the time consuming task of finding another access vein for puncture. Thus, the above-described system reduces patient trauma, reduces the chance of patient infection and saves valuable time of medical personnel. A system such as described above is shown in FIG. 1.

In U.S. Pat. Nos. 4,034,754 and 4,105,029 there is shown another system for the sequential administration of two medical liquids. There, the first medical liquid is delivered to a drip chamber through a drop former having a restricted lumen as compared to the drop formers in the administration set referred to above by product codes. Such a restricted lumen drop former increases the drop rate in the drip chamber, which a nurse uses to determine flow rate. Some nurses prefer a higher drop rate in order to make a quicker, more accurate determination of flow rate. This is especially true where two or more medical liquid sources are being used because one liquid source, such as a dextrose or saline solution, may be delivered at a slow rate such as, for example, 60 ml per hour, to simply keep the vein open for the addition of further medication from a second solution container.

The restricted drop former does, however, make this system suseptible to development of a suction pressure head in the tubing downstream from the drip chamber, especially when a higher fluid flow rate of the second liquid source is desired. The '754 and '029 patents disclose a solution to this problem, whereby constricted lumen tubing is employed downstream of the tubing set connection leading to the secondary medical liquid source. The downstream constricted-lumen tubing reduces the suction pressure head and eliminates the problem of drawing air through the tubing into the patient's venous system.

In each of the systems described above, the secondary medical liquid container is disposed at a higher elevation than the first liquid container. Since it has a higher upstream pressure, or head, the secondary liquid is delivered upon opening of its associated flow path, stopping delivery of the first solution. After the second medical liquid is delivered, the first medical liquid again begins to flow, keeping the patient's vein open.

One disadvantage to these systems is that the flow rates of the first and second medical liquids cannot be independently controlled. For instance, the second medical liquid is most often delivered at a higher flow rate than the first medical liquid, such as, for example, 300 ml per hour. After the second medical liquid is delivered, the first medical liquid is delivered at the same higher rate at which the second medical liquid had been delivered. Although not typically posing a danger to the patient, the first medical liquid such as dextrose or saline solution will then be rapidly infused in the patient. The nurse must therefore monitor the system fairly closely so that he or she may reduce the flow rate of the first liquid after the second liquid is delivered or else return to the patient's bedside before the first solution container is emptied in order to replace that container.

If the first medical liquid is entirely delivered before the nurse returns there is a strong possibility that the accessed peripheral vein will collapse. While not dangerous, this situation will necessitate making another venous puncture for delivery of further medical liquid.

Various attempts have been made to develop systems for the independently controlled sequential administration of two medical liquids, so that upon exhaustion of the second liquid source the first source will flow at the pre-selected slower flow rate. Such systems are shown, for example, in U.S. Pat. Nos. 4,219,022; 4,236,515; 4,258,712; 4,237,880; 4,250,879; 4,252,116; 4,256,104; 4,256,105; and 4,324,238.

These disclosures are all directed toward systems to enable independently controlled flow rates from two separate medical liquid sources. All are directed toward systems which include an air barrier and/or a liquid sequencing valve of somewhat complex construction. At least some of the systems shown in these patents, such as shown for example, in U.S. Pat. No. 4,256,104, include a critical failure mode inherent in the system configuration. Stated differently, upon failure of the air barrier means, such as caused by a pin hole size leak in a hydrophillic filter membrane, all protection against patient air embolism is lost and air will in all likelihood be forced into the patient, due to factors such as a large remaining head pressure upstream of the air source and a large suction head pressure downstream of the air source. The failure mode is critical because failure of the system is likely to result in serious patient injury or death.

SUMMARY OF THE INVENTION

The present invention is directed to a medical liquid administration set for the sequential administration of two medical liquid sources which can be delivered at different liquid flow rates without readjustment of the administration set. The present invention is directed toward such an administration set which does not include a critical failure mode. The administration set of the present invention permits delivery of the second medical liquid at a rate equal to or greater than the first medical liquid delivery rate. Both rates may be set by the time delivery of the second medical liquid is initiated so that, upon completion of the second medical liquid administration, flow of the first medical liquid automatically begins at its earlier, predetermined flow rate.

Figure 2:
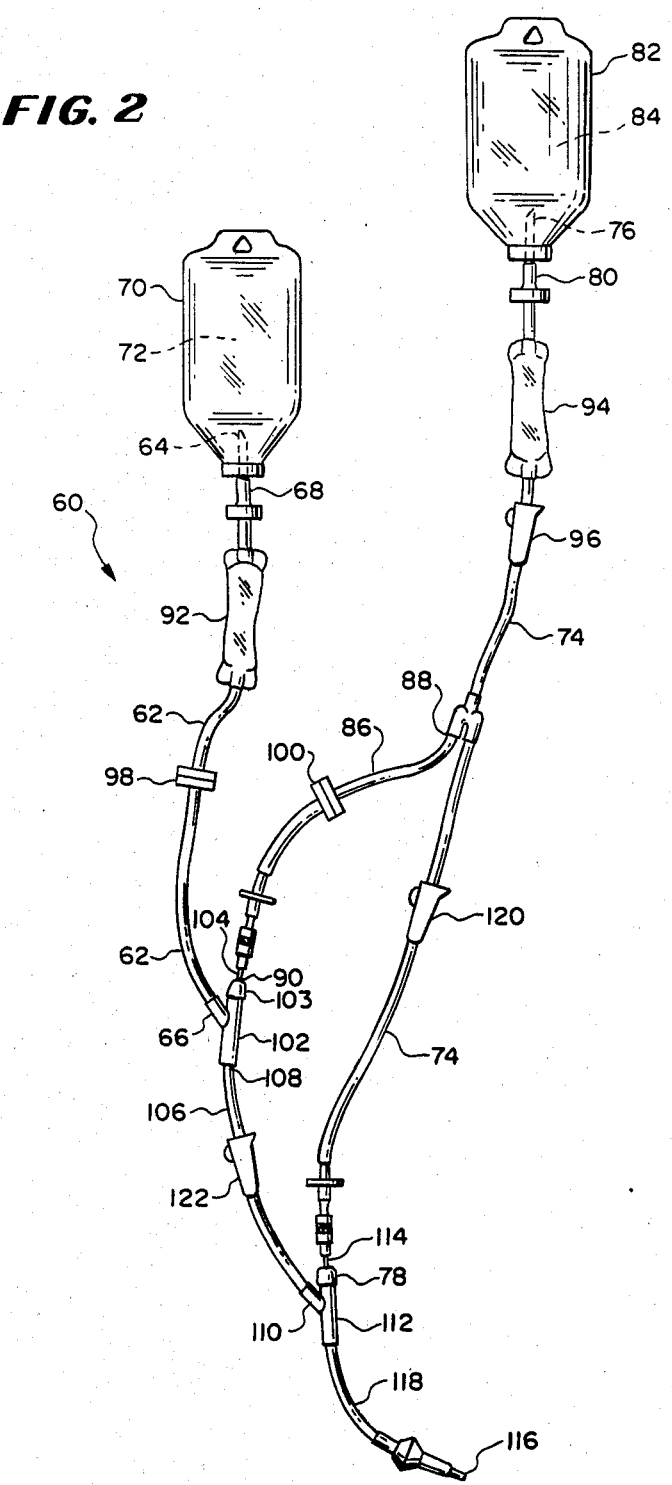
FIG. 2 is a front elevational view of the medical liquid administration set of the present invention.

Referring to FIG. 2, the medical liquid administration set 60 of the invention includes a first conduit 62 for connection to a first liquid source, a second conduit 74 for connection to a second liquid source and a cross-over branch 86 connecting the second conduit 74 with the distal end 66 of the first conduit 62. A common conduit 106 extends downstream of the connection between the cross-over branch and the first conduit. The common conduit and the second conduit enter into flow communication at their distal ends 110, 78. A liquid outlet 116 is disposed at the distal ends of the common and second conduits, for delivery to a patient by means of attachment to, for example, an intravenous catheter. A one-way valve 100 is disposed in the cross-over branch, permitting liquid flow only in the direction toward the common conduit 106. A one-way valve 98 is also disposed in the first conduit, permitting liquid flow only from the first medical liquid source. The administration set includes two separately adjustable liquid delivery rate control means 120, 122. One is disposed on the common conduit to limit the maximum delivery rate of the first medical liquid. The other is disposed on the second conduit and, together with the first control means, determines the maximum delivery rate of the second medical liquid. In operation, the distal ends 110, 78 of the common conduit and the second conduit are disposed at an elevation not substantially higher than the liquid outlet 116. This may be accomplished by limiting the length of the conduit between the distal ends of the common and second conduits and the liquid outlet.

DETAILED DESCRIPTION OF THE PREFERRED EMBODIMENT

Figure 1:
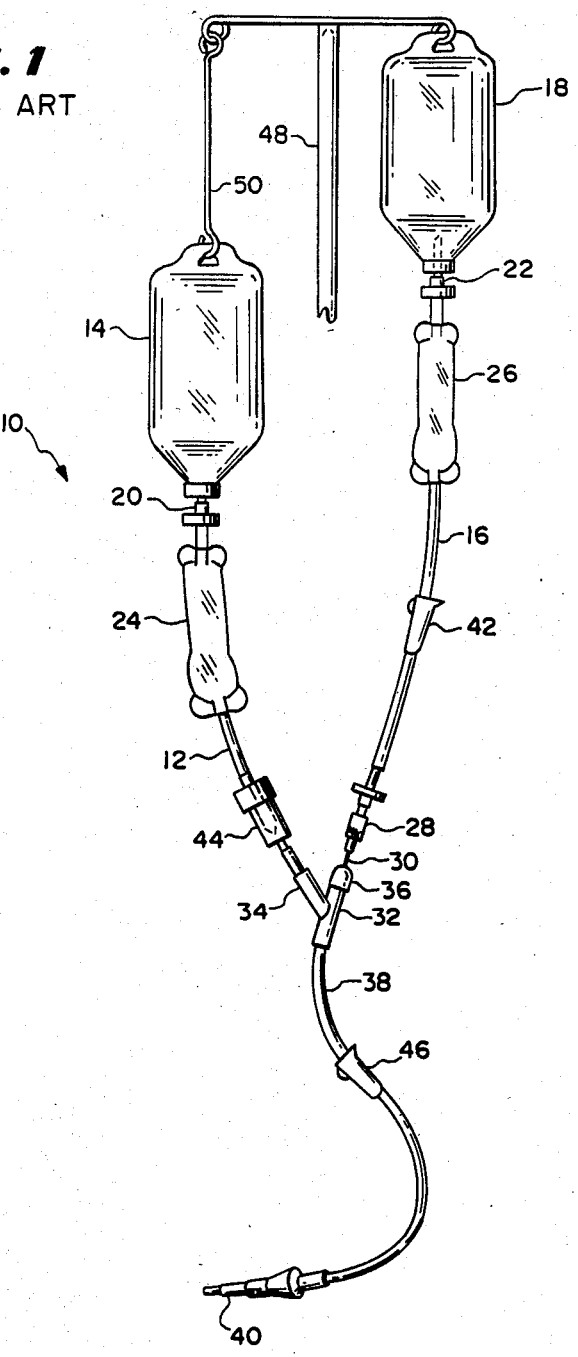
FIG. 1 is a front elevational view of a prior art system for delivering two medical liquid sources.

Referring to the drawings, FIG. 1 illustrates a prior art system for administering two medical liquids, without independent flow rate control. The prior art administration set 10 includes a first liquid tube 12 which is connected to a first liquid container 14 and a second liquid tube 16 which is connected to a second liquid container 18. The first and second liquid tubes 12, 16 include spikes 20, 22, respectively, for access to the solution containers, and drip chambers 24, 26, respectively, for determination of liquid flow rate. The distal end 28 of the second liquid tube 16 has a needle 30 which is inserted into an injection site 32. The injection site 32 serves as the distal ends 34, 36 of the first and second liquid tubes 12, 16, respectively. A common liquid tube 38 extends downstream of the injection site 32 to a needle adapter 40 and an on-off clamp 42 is mounted on the second liquid tube 16. A one-way valve 44 is mounted on the first liquid tube 12. A roller clamp 46 for adjusting flow rate is disposed on the common liquid tube 38. The roller clamp 46 must be used to control the flow rate of both the first and second medical liquids from the first and second liquid containers 14, 18, respectively.

The liquid containers 14, 18 are mounted on a stand 48. A metal hanger 50 ensures that the first liquid container 14 is disposed at an elevation lower than the second liquid container 18. Because of the higher elevation, the second liquid has a higher head and once the on-off clamp 42 is turned to the on position, delivery of the second medical liquid begins immediately, shutting off flow of the first medical liquid. The check valve 44 prevents back-up flow of the second medical liquid upstream of the valve 44 in the first liquid tube 12.

Air aspiration into the patient causing air embolism is not a factor with this system. As the second liquid container empties, the second liquid level lowers through the second liquid tube 16. When the first liquid thus regains a higher elevation, the first liquid then begins to flow once more.

By the time air above the second liquid in the second liquid tube 16 reaches the injection site 32, there is no greater level of liquid in the first liquid tube 12. Thus, there is no head pressure to force air into the common tube 38, which might otherwise be delivered to the patient.

The presence or absence of an operational mode in two-source medical liquid administration sets which raises the possibility of air embolism is governed by a number of interrelated factors, and is not always controlled by a single quantitative design value. For example, in the prior art system described above, head pressure above the common tube 38 is extremely low or nonexistent by the time air has the chance of reaching the common liquid tube 38. As described in U.S. Pat. Nos. 4,034,754 and 4,105,029, air aspiration is also determined by the suction pressure head generated downstream of any air access site. Generally, the longer the conduit downstream of the air access site, the greater the suction pressure head. Also, the size of the conduit lumen is a factor in determining whether there is a real chance of air embolism in the patient.

Another factor in determining whether there is a danger of patient air embolism is the pressure downstream of the administration set, i.e., the patient's venous pressure. Although some critically ill patients exhibit negative central venous pressure close to the heart, negative venous pressure is not found in the patient's limbs. In most cases administration sets are connected to the patient's venous system at the patient's arm, so that pressure downstream of an administration set will be positive.

Emphasizing that it is the interrelationship of these factors that will determine the possibility of air embolism, it has been found that the administration set described and claimed below will enable independent flow adjustment of two different medical liquid sources to a patient without readjustment of the set, without danger of patient air embolism and without a critical failure mode.

The medical liquid administration set 60 of the present invention is illustrated in FIG. 2. The set 60 includes a first conduit 62 including proximal and distal ends 64, 66, respectively. The proximal end 64 may include a spike or cannula 68 for insertion into a first medical liquid container 70. The first medical liquid 72 may be, for example, a dextrose or saline solution. The set 60 includes a second conduit 74 including second conduit proximal and distal ends 76, 78, respectively. The proximal end 76 may include a spike or cannula 80 for insertion into a second medical liquid container 82 containing a second liquid 84. Most commonly, the second liquid 84 will be a drug other than dextrose or saline, although this is not necessary. If the second container 82 is not air-dependent, such as the non-air-dependent, closed, flexible MINI-BAG TM container sold by Travenol Laboratories, the chance of air aspiration is virtually eliminated. However, with such a closed system, some of the second liquid 84 will remain in most of the second conduit 74 and not be delivered to the patient. If it is desired to deliver virtually all of the second liquid 84, then there should be a filtered air access into the second container 82. This can be accomplished by using a spike 80 having a filtered air access port (not shown) to the environment.

The set further includes a cross-over branch 86 having an upstream end 88 in communication with the second conduit 74 between said second conduit proximal and distal ends 76, 78. The cross-over branch 86 includes a downstream end 90 in communication with the first conduit 62 at the distal end 66 of the first conduit 62.

Each of the first and second conduits 62, 74 includes a drip chamber 92, 94, respectively, which allows a nurse to count drops to determine fluid flow rate. The second conduit 74 also preferably includes an on-off clamp such as an on-off roller clamp 96 or a slide clamp.

The first conduit 62 includes a one-way valve 98 which permits liquid to flow only in the direction from the first conduit proximal end 64 to the first conduit distal end 66. The cross over branch 86 also includes a one-way valve 100, which permits liquid flow only in the direction from the upstream end 88 to the downstream end 90.

The distal end 66 of the first conduit may be determined by a "Y"-shaped connector such as an injection site 102, having a latex situs 103 into which a needle 104 forming the downstream end 90 of the cross over branch 86 is inserted. Connected to and downstream of the injection site 102 is a common conduit 106 including a proximal end 108 in communication with both the distal end 66 of the first conduit 62 and the downstream end 90 of the cross over branch 86. The proximal end 108 of the common conduit 106 may be attached to the injection site 102.

The common conduit 106 also includes a distal end 110 in communication with the second conduit 74 at the second conduit distal end 78. The common conduit may include a second "Y"-shaped connector such as an injection site 112 into which a second needle 114 forming the distal end 78 of the second conduit 74 is inserted. The second "Y" or injection site 112 thus defines the distal ends 78, 110 of the second and common conduits 74, 106, respectively.

A liquid outlet 116 is disclosed downstream of the distal ends of the common and second conduits, 106, 74. As shown in FIG. 2, the liquid outlet 116 may be separated from the second injection site 112 by a tubing segment 118. As will be seen below, it is useful to keep the tubing segment 118 as short as possible. Ideally, the outlet 116 is at the downstream end of the injection site 112, without any tubing segment therebetween. The outlet 116, although downstream of the distal ends 78, 110, is then essentially at the distal ends 78, 110.

All the conduit 62, 74, 106, the cross-over branch 86 and the tubing segment 118 may be made of flexible material, such as well known transparent PVC tubing.

Adjustable liquid delivery rate control means are disposed on both the common and second conduits. These control means may comprise roller clamps 120, 122 which may be manually adjusted to control the lumen in the second conduit 74 and common conduit 106, respectively.

Figure 3:
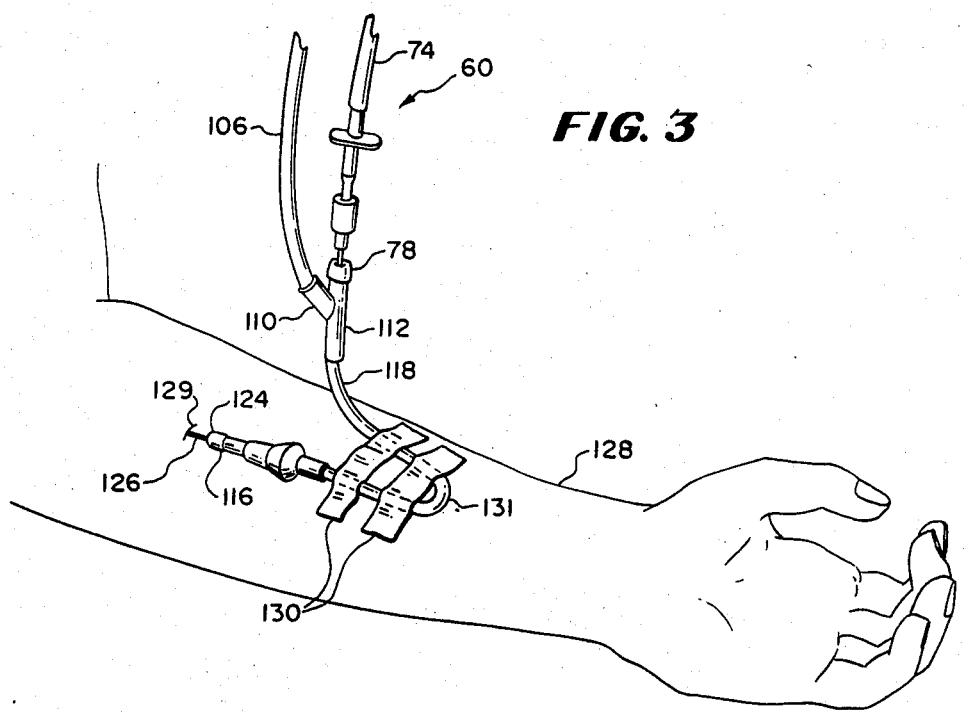
FIG. 3 is a fragmentary perspective view of the liquid outlet of the administration set shown in FIG. 2, secured to a venous catheter for liquid delivery to a patient.

Referring now to FIG. 3, there is illustrated the second injection site 112 and liquid outlet 116 as secured to a patient for intravenous delivery of medical liquids. The outlet 116 may include a Luer taper for connection to the hub 124 of a flexible intravenous catheter 126. The catheter, such as a FLASH-CATH catheter sold by Travenol Laboratories, Inc., is inserted into the patient's venous system in a separate procedure. After connection of the outlet 116 to the catheter 126, the set 60 is secured to the patient's arm 128.

FIG. 3 illustrates a common means for securing an administration set to a patient. Usually, the solution containers 70, 82 are mounted on a stand (not shown) to the side and rear of the patient's bed. The set 60 is secured by means such as medical grade adhesive tape 130 to form a loop 131 on the patient's arm 128. The catheter 126 is inserted into the vein toward the patient's shoulder. The method described above for securing a set to a patient is used almost universally in hospitals in the United States. Without securement, the catheter 126 will slip out of the patient's arm.

Such a means of securing the set 60 forces the distal ends 78, 110 of the second and common conduits 74, 106, respectively, to be disposed at an elevation which is lower than or equal to, or not substantially higher than, the liquid outlet 116. The object here is to minimize the suction head pressure below the second injection site 112. It is anticipated that the tubing segment 118, if included at all, will be short, such as, for example, no greater than about four inches in length, to minimize any suction head pressure.

In operation, the flow path of the first medical liquid 72 includes the first conduit 62 and the common conduit 106. The liquid delivery rate of the first medical liquid 72 is determined by the roller clamp 122. When a second medical liquid 84 is to be administered, the second conduit 74 and the cross-over branch 86, which may be manufactured as a unit separate from the first conduit 62 and common conduit 106, are primed in the usual manner after inserting the spike 80 into the second container 82. The needles 114, 104, of the second conduit 74 and cross-over branch 86 are then inserted into the injection sites 112, 102.

When the on-off clamp 96 is turned to the open position and the second conduit roller clamp 120 is in an open position, the second medical liquid 84 begins to flow because the second medical liquid container 82 is at a higher elevation than the first container 70, giving the second medical liquid 84 a greater head pressure.

The second medical liquid 84 flows through the second conduit 74 until it reaches the upstream end 88 of the cross-over branch 86. Some of the liquid 84 continues down the second conduit 74 toward its distal end 78. A portion of the liquid continues down the cross-over branch 86 and into the common conduit 106. The total delivery rate of the second medical liquid 84 is determined by both roller clamps 120, 122. As an example only, the total delivery rate may be 300 ml per hour. The desired flow rate of the second liquid 84 may be set by adjusting the second conduit roller clamp 120 until the proper drop rate in the drip chamber 94 is achieved. The common roller clamp 122 need not be readjusted. The one-way valve 98 on the first conduit 62 prevents the second liquid 84 from backing up into the first liquid container 70.

Upon exhaustion of the second medical liquid source, the first medical liquid 72 once again begins to flow. The flow rate will be at the earlier established rate determined by the common conduit roller clamp 122, without regard to the previous flow rate of the second medical liquid 84. Unlike the prior art system shown in FIG. 1, the common roller clamp 122 need not now be readjusted. The common clamp 122 enforces the typically slower flow rate which was set before delivery of the second liquid 84.

The one-way valve 100 on the cross-over branch 86 prevents the first liquid 72 from backing up to the upstream end 88 of the cross over branch 86. Some liquid will remain in the second conduit 74 above the injection site 112. Because there is no suction head pressure below the injection site 112, any air in the second conduit 74 which might reach the injection site 112 is prevented from being drawn through the outlet 116.

The prevention of air aspiration into the tubing segment 118 from the second conduit 74 is further assured by the catheter 126, which has a lumen that is narrower than those of the common conduit 106 or the second conduit 74. Further assurance is provided by the accessed vein lumen, and by the patient's own positive venous pressure at the puncture site 129.

The cross-over branch 86 is necessary in order to establish a sufficient differential pressure to close the one-way valve 98 in the first conduit 62. Without the cross over branch 86, back pressure would be applied at the injection site 112 near the patient. This back pressure from the second liquid 84 would need to be urged against the roller clamp 120, which in virtually all cases is too restricted (e.g., 60 ml per hour) to permit closure of the one-way valve 98. Thus, both liquids would be delivered at the same time, which is undesirable.

Figure 4:
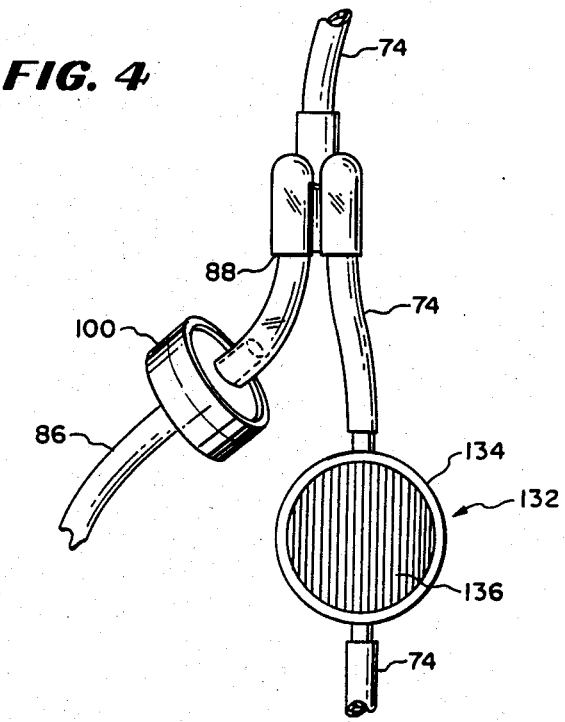
FIG. 4 is a fragmentary front elevational view of an alternate embodiment of the invention, including a hydrophillic filter membrane in the second conduit, below the cross-over branch.

Referring now to FIG. 4, there is illustrated an addition to the set 60 of the invention. Gas blocking means such as a hydrophillic filter 132 is disposed in the second conduit 74, above the injection site 112 and preferably below the upstream end 88 of the cross over branch 86. The filter 132 includes a rigid plastic housing 134 with a hydrophillic filter membrane 136 mounted therein, spanning the flow path in the second conduit 74. The hydrophillic filter 132 shown in FIG. 4 provides a perhaps unnecessary extra safety factor which should be used only in addition to, not as a substitute for, the system described above.

While various embodiments and features have been described in detail herein and shown in the accompanying drawings, it will be evident that various further modifications are possible without departing from the scope of the invention.

What is claimed is:

1. A medical liquid administration set for the sequential administration of two medical liquid sources, which can be delivered at different liquid flow rates without readjustment of the set, the administration set comprising:
   (a) a first conduit including a proximal end for connection to a first liquid sources, and a distal end;
   (b) a second conduit including a proximal end for connection to a second liquid source, and a distal end, said second conduit being devoid of any gas barrier means;
   (c) a cross over branch having an upstream end in communication with said second conduit between said proximal and distal ends of said second conduit, and a downstream end in communication with said first conduit at said distal end of said first conduit, said cross over branch being devoid of any gas barrier means;
   (d) a common conduit including a proximal end in communication with both said distal end of said first conduit and said downstream end of said cross over branch, and further including a common conduit distal end, said common conduit distal end being in communication with said second conduit at said second conduit distal end, said common conduit being devoid of any gas barrier means;
   (e) a liquid outlet located no greater than about four inches downstream of distal ends of both said common conduit and said second conduit, there being no gas barrier means between said distal ends of both said common conduit and said second conduit and said liquid outlet;
   (f) a one-way valve in said cross over branch permitting liquid flow only in the direction from said upstream end to said downstream end;
   (g) a one-way valve in said first conduit permitting liquid flow only in the direction from said first conduit proximal end to said first conduit distal end;
   (h) adjustable liquid delivery rate control means on said second conduit, downstream of said upstream end;
   (j) whereby in operation said distal ends of said common conduit and said second conduit are disposed at an elevation lower than, equal to or not substantially higher than said liquid outlet.

2. The medical liquid administration set as in claim 1, wherein said common and second conduit adjustable liquid delivery rate control means comprise roller clamps.

3. The medical liquid administration set as in claim 1, further comprising an on-off clamp on said second conduit, upstream of said cross-over branch upstream end.

4. The medical liquid administration set as in claim 1, further including a venous access catheter connected to said liquid outlet, said catheter having a lumen which is narrower than lumens of said common and second conduits.

5. The medical liquid administration set as in claim 1, wherein said first and second conduit proximal ends include spikes for connection to containers for the liquid sources, and further wherein at least said second conduit spike includes a filtered air access port between the associated container and the environment.

6. The medical liquid administration set as in claim 1, wherein said first and second conduit proximal ends include spikes for connection to containers for the liquid sources, and further wherein at least said second conduit spike includes a filtered air access port between the associated container and the environment.

7. The medical liquid administration set as in claim 1, wherein said common conduit includes a "Y"-connector defining said common and second conduit distal ends, and further wherein a downstream end of said "Y"-connector defines said liquid outlet.

8. A medical liquid administration set for the sequential administration of two medical liquid sources, which can be delivered at different liquid flow rates without readjustment of the set, the administration set comprising:
  (a) a first conduit including a proximal end for connection to a first liquid source, and a distal end;
  (b) a second conduit including a proximal end for connection to a second liquid source, and a distal end;
  (c) a cross over branch having an upstream end in communication with said second conduit between said proximal and distal ends of said second conduit, and a downstream end in communication with said first conduit at said distal end, said second conduit being devoid of any gas barrier means of said first conduit;
  (d) a common conduit including a proximal end in communication with both said distal end of said first conduit and said downstream end of said cross over branch, and further including a common conduit distal end, said common conduit distal end being in communication with said second conduit at said second conduit distal end, said common conduit being devoid of any gas barrier means;
  (e) a liquid outlet no greater than about four inches downstream of said distal ends of both said common conduit and said second conduit;
  (f) a one-way valve in said cross-over branch permitting liquid flow only in the direction from said upstream end to said downstream end;
  (g) a one-way valve in said first conduit permitting liquid flow only in the direction from said first conduit proximal end to said first conduit distal end;
  (h) adjustable liquid delivery rate control means on said common conduit; and
  (i) adjustable liquid delivery rate control means on said second conduit.

9. The medical liquid administration set as in claim 8, wherein said common and second conduit adjustable liquid delivery rate control means comprise roller clamps.

10. The medical liquid administration set as in claim 8, further including a venous access catheter connected to said liquid outlet, said catheter having a lumen which is narrower than lumens of said common and second conduits.

11. The medical liquid administration set as in claim 8, further comprising an on-off clamp on said second conduit, upstream of said cross-over branch upstream end.

12. The medical liquid administration set as in claim 1, wherein said common conduit includes a "Y"-connector defining said common and second conduit distal ends, and further wherein a downstream end of said "Y"-connector defines said liquid outlet.

* * * * *